United States Patent [19]

Patel

[11] 4,245,655
[45] Jan. 20, 1981

[54] BLOOD COLLECTION DEVICE
[75] Inventor: Bhupendra C. Patel, Elgin, Ill.
[73] Assignee: The Kendall Company, Boston, Mass.
[21] Appl. No.: 55,111
[22] Filed: Jul. 5, 1979

Related U.S. Application Data

[63] Continuation of Ser. No. 829,856, Sep. 1, 1977, abandoned.

[51] Int. Cl.³ .................................................. A61B 5/14
[52] U.S. Cl. ........................................ 128/765; 128/767
[58] Field of Search ............... 128/763, 765, 766, 767, 128/215, 216, 218 P, 218 R, 220

[56] References Cited

U.S. PATENT DOCUMENTS

| 105,776 | 7/1870 | Cavanaugh | 73/425.6 |
|---|---|---|---|
| 2,690,179 | 9/1954 | Fox | 128/216 |
| 2,907,326 | 10/1959 | Berande | 128/765 |
| 3,785,367 | 1/1974 | Fortcox et al. | 128/767 X |
| 4,073,288 | 2/1978 | Chapman | 128/765 |

FOREIGN PATENT DOCUMENTS

296188  1/1954  Switzerland ............................ 128/216

Primary Examiner—John D. Yasko
Attorney, Agent, or Firm—Powell L. Sprunger

[57] ABSTRACT

A blood collection device comprising, a syringe having a barrell defining a chamber, and a plunger having distal end received in the chamber. The device has a collection bag of flexible material secured in the distal portion of the syringe chamber, and having walls defining a collection chamber closed to the remainder of the syringe chamber, with the syringe having an opening communicating with the syringe chamber outside the collection bag. The device has a hollow needle for connection to a distal portion of the syringe in communication with the bag chamber, such that the bag expands responsive to blood pressure and passage of blood into the bag chamber.

3 Claims, 5 Drawing Figures

BLOOD COLLECTION DEVICE

This is a continuation, of application Ser. No. 829,856 filed Sept. 1, 1977 now abandoned.

BACKGROUND OF THE INVENTION

The present invention relates to sampling devices, and more particularly to devices for collecting arterial blood.

In recent years, gas analysis of arterial blood has become one of the most important laboratory tests in the management of patients with respiratory and metabolic disorders. However, the collection of a satisfactory arterial blood sample from a patient for analysis has posed a number of difficulties. Initially, in some patients it may be somewhat difficult to ascertain whether the collection device has received arterial or venous blood without measuring for the relatively high arterial pressures during collection. Second, the collection device should minimize contact of the blood sample with air since the air may affect the results of gas analysis. It is also desirable that the sample should not be collected in the presence of a vacuum, since it is believed that the vacuum may modify the gas characteristics of the sample. Finally, the device must prevent coagulation of the blood sample, and should be in a suitable form to permit closure of the sample to air and chilling during the period of time between collection and analysis.

In the past, plastic and glass syringes with a needle have been commonly used to collect the samples. However, the plastic syringes have proven deficient for such purposes due to the relatively high resistance between the syringe plunger and barrel. The plunger resistance in such plastic syringes prevents movement of the plunger responsive to arterial pressure alone, and requires that the plunger be manually withdrawn, thus creating an undesirable vacuum in the syringe chamber during collection. Further, since the plungers of plastic syringes are not sufficiently mobile to move under arterial pressure, they do not provide an indication whether arterial or venous blood is being collected. Although the plungers of the glass syringes may be used to detect arterial pressure, the glass syringes are relatively expensive, and if the nurse does not exercise sufficient care, the plunger may fall out of the syringe during arterial collection.

SUMMARY OF THE INVENTION

A principal feature of the present invention is the provision of a device for collecting arterial blood in an improved manner.

The collection device of the present invention comprises, a syringe having a barrel defining a chamber, and a plunger having a distal end received in the chamber. The device has a collection bag of flexible material secured in a distal portion of the syringe chamber, and having walls defining a collection chamber closed to the remainder of the syringe chamber. The syringe has opening means communicating with the syringe chamber outside the collection bag. The device has a hollow needle for connection to a distal portion of the syringe in communication with the bag chamber.

A feature of the present invention is that the collection bag may be compressed into a configuration of reduced dimensions, and may be expanded with the opening means closed in order to draw an anti-coagulant of blood into the bag chamber.

Another feature of the invention is that the plunger may be pushed into the syringe chamber with the opening means open in order to expel the anti-coagulant of blood from the bag chamber and compress the bag into a configuration of reduced dimensions.

Thus, a feature of the invention is that the bag chamber may be flushed with an anti-coagulant of blood preparatory to receiving an arterial blood sample.

A further feature of the invention is that the syringe plunger expels substantially all the air from the bag chamber in order to minimize the contact of air with the collected blood sample.

Still another feature of the invention is that the plunger may be withdrawn from the bag with the opening means open in order to increase the size of the syringe chamber without expansion of the bag.

Thus, another feature of the invention is that the opening means may be utilized to selectively expand the collection bag or the size of the syringe chamber without expansion of the bag.

Yet another feature of the invention is that the bag expands from its configuration of reduced dimensions responsive to arterial blood pressure and flow of arterial blood into the bag chamber.

Still another feature of the invention is that the collection bag limits the quantity of arterial blood which passes into the bag chamber.

Yet another feature of the invention is that the sample may be collected in the bag chamber without subjecting the sample to a vacuum.

Further features will become more fully apparent in the following description of the embodiments of this invention and from the appended claims.

DESCRIPTION OF THE PREFERRED EMBODIMENTS

Figure 1:
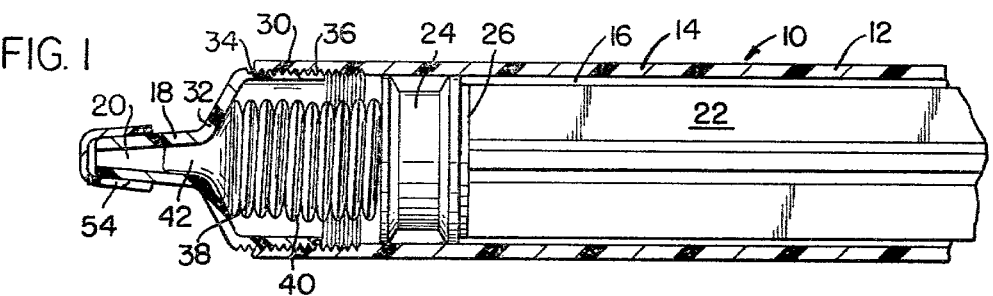
FIG. 1 is a fragmentary elevational view, taken partly in section, of a blood collection device of the present invention illustrating a cap as attached to a tip of a syringe in the device.
Figure 2:
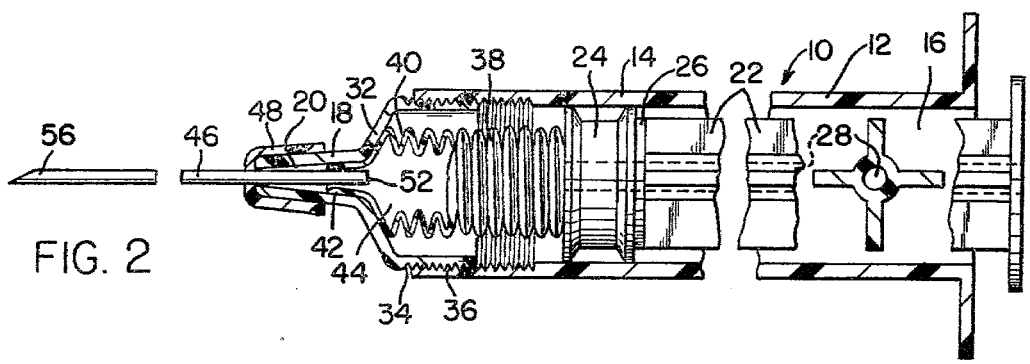
FIG. 2 is a fragmentary elevational view, taken partly in section, of the device of FIG. 1 illustrating a needle as attached to the syringe tip.
Figure 4:
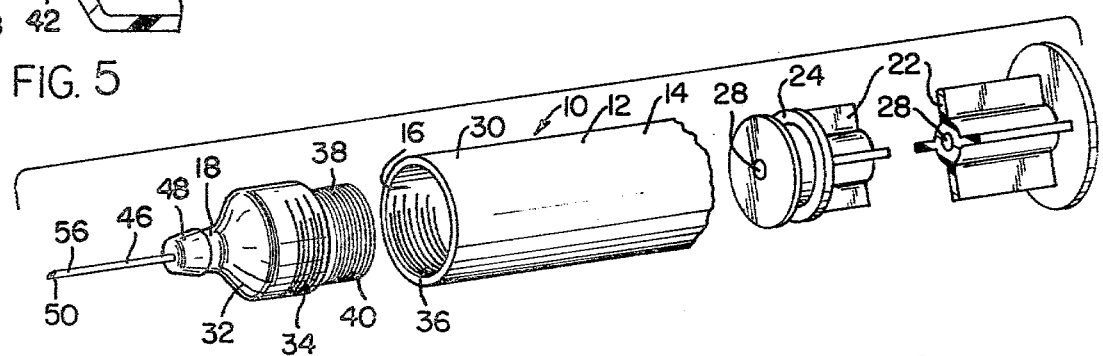
FIG. 4 is an exploded fragmentary perspective view of the collection device of the present invention.

Referring now to FIGS. 1, 2, and 4, there is shown an arterial blood collection device generally designated 10 comprising a syringe 12 having a barrel 14 defining a chamber 16 of the syringe and a tip 18 at a distal portion of the syringe having a channel 20. The syringe 12 has an elongated plunger 22 having a plug 24 of compressible material, such as rubber, at a distal end 26 of the plunger 22, with the plunger plug 24 being slidably received in the syringe chamber 16 and sealingly engaging against the inner surface of the syringe barrel 14. As shown, the plunger 22 has an elongated passageway 28 extending through the plunger and communicating between the syringe chamber 16 and the atmosphere outside the plunger when the plunger plug 24 is received in the syringe chamber. In one form, as shown, the syringe barrel 14 has a first proximal cylindrical portion 30 defining a major portion of the syringe chamber 16, and a second distal portion 32 defining the syringe tip 18 and a distal portion of the chamber 16, with the distal barrel portion 32 being releasably attached to the proximal barrel portion 30 by means of cooperating threads 34 and 36, respectively, at the outer proximal surface of the distal barrel portion 32 and the inner distal surface of the proximal barrel portion 30.

The device 10 also has a collection bag 38 of flexible material, such as polyethylene or polyvinyl chloride. The bag 38 has expansible side walls 40 having a distal portion 42 secured to the distal barrel portion 32 and defining a collection chamber 44 communicating with the tip channel 20 and closed to the remainder of the syringe chamber 16.

The device 10 has a hollow needle 46 having a tip 56, and a hub 48 for releasably attaching the needle 46 to the syringe tip 18 with a lumen 50 in the needle 46 communicating with the bag chamber 44. If desired, the needle 46 may have an inner portion 52 positioned in the tip channel 20 when the needle 46 is attached to the syringe tip 18. As shown, the device 10 also has a cap 54 which may be releasably attached to the syringe tip 18 to close the tip channel 20 when the needle 46 is removed from the syringe.

In use of the device to collect an arterial blood sample, the cap 54 may be removed from the syringe tip 18, and the needle 46 may be attached to the syringe tip, as shown in FIG. 2. Next, the syringe plunger 22 may be pushed into the syringe chamber 16 with the passageway 28 open in order to compress the collection bag 38 if not previously in a configuration of reduced dimensions. The user may place his thumb over the outer end of the barrel passageway 28 in order to close the syringe chamber 16, and the tip 56 of the needle 46 may be placed in a solution of anti-coagulant of blood, such as heparin. The syringe plunger is then withdrawn with the passageway 28 closed in order to create a partial vacuum in the syringe chamber 16 and expand the bag 38 to draw the anti-coagulant into the bag chamber 44. After a sufficient quantity of the anti-coagulant has passed into the bag chamber 44, the passageway 28 may be released by the user's thumb, and the syringe plunger 22 may be pushed into the syringe chamber in order to compress the bag 38 and expel the anti-coagulant from the bag chamber through the needle 46. In this manner, the needle and bag are flushed with the anti-coagulant of blood in order to prevent coagulation of the arterial blood sample as it passes through the needle into the chamber of the bag. At this time, the bag 38 is sufficiently compressed to remove substantially all of the air in the bag chamber, and the syringe plunger is withdrawn with the passageway 28 open in order to position the plunger plug 24 at a proximal portion of the syringe chamber 16 without expansion of the bag. Thus, the collection bag 38 has been compressed into a configuration of reduced dimensions at a distal portion of the syringe chamber 16 and the syringe chamber 16 has been enlarged to permit subsequent expansion of the collection bag in the syringe chamber, as will be described below.

Figure 3:
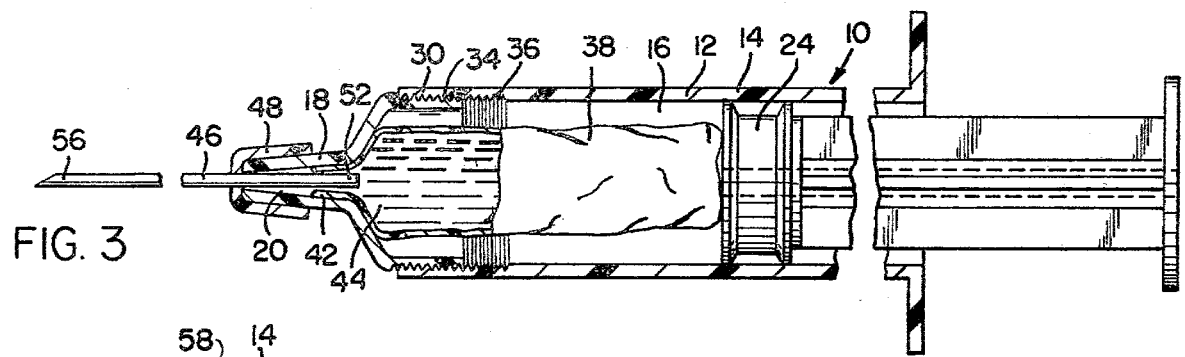
FIG. 3 is a fragmentary elevational view, taken partly in section, of the collection device illustrating a collection bag as extended during passage of arterial blood into the bag.

The nurse may position the needle tip 56 in the patient's artery in order to establish communication with the bag chamber 44 through the needle. At this time, the arterial blood begins to flow through the needle 46 into the bag chamber, causing expansion of the bag responsive to the arterial pressure and the flow of arterial blood into the bag chamber 44 until the bag has been filled with the arterial sample, as illustrated in FIG. 3. Thus, the bag 38 expands proximally from its configuration of reduced dimensions to a second configuration of enlarged dimensions in the syringe chamber 16. In this manner, the arterial sample is obtained while minimizing contact of air with the sample and without subjecting the sample to a vacuum. Moreover, the bag 38 limits the quantity of the collected blood sample, and the anti-coagulant in the needle and bag chamber 44 prevents the coagulation of blood.

After the sample has been taken, the needle may be removed from the patient and subsequently from the syringe, after which the cap 54 may be attached to the syringe tip 18 in order to close the tip channel 20 and the bag chamber 44. Finally, the collection device containing the sample may be forwarded to the laboratory for gas analysis of the blood. At that time, the cap 54 may be removed from the syringe tip 18, and the plunger may be pushed into the syringe chamber 16 with the passageway 28 open in order to expel the blood sample from the bag chamber 44.

After the blood sample has been pumped from the bag chamber 44, the distal barrel portion 32 containing the collection bag 38 may be removed from the remainder of the syringe, and the bag containing portion of the syringe may be discarded. Thus, another distal barrel portion 32 containing a new bag may be attached to the proximal barrel portion 30 by the cooperating threads 34 and 36 in order to reuse a major portion of the syringe and minimize the effective cost of the device. Further, if desired, the collection bag 38 may be made from a relatively rigid plastic such that it expands at a predetermined pressure above the normal venous pressure in order to prevent the inadvertent collection of venous blood. Thus, such a bag would expand responsive to the larger arterial blood pressures, and in this manner the device limits the collection to an arterial blood sample in the bag chamber 44.

Figure 5:
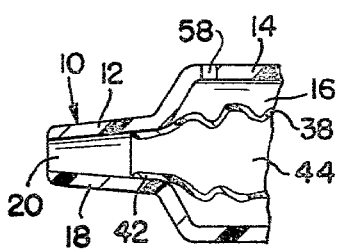
FIG. 5 is a fragmentary sectional view of another embodiment of the device of the present invention.

Another embodiment of the present invention is illustrated in FIG. 5, in which like reference numerals designate like parts. In this embodiment, the syringe barrel 14 is of one-piece construction, and the barrel 14 has an aperture 58 communicating between the atmosphere and the syringe chamber 16 outside the collection bag 38. It will be apparent that the aperture 58 may be selectively opened and closed by the user's finger in order to open and close the syringe chamber 16 and accomplish the results previously discussed in connection with the plunger passageway 28 in the embodiments of FIGS. 1-4. Thus, the aperture 58 is closed when it is desired to expand the collection bag 38 through use of the plunger, and the aperture 58 may be opened when it is desired to withdraw the plunger without expansion of the bag.

The foregoing detailed description is given for clearness of understanding only, and no unnecessary limitations should be understood therefrom, as modifications will be obvious to those skilled in the art.

I claim:

1. A method of collecting blood with a collection device of the type comprising, (a) a syringe having a barrel defining a chamber, a plunger having a distal end received in the chamber, and unimpeded opening means for permitting the passage of air including a first aperture communicating with the syringe chamber outside the collection bag and a second aperture communicating with the atmosphere which may be selectively closed by the user, (b) a collection bag of flexible material secured in a distal portion of the syringe chamber and having walls defining a collection chamber closed to the remainder of the syringe chamber, and (c) a hollow needle for connection to a distal portion of the syringe in communication with the collection chamber, said method comprising the steps of:

placing the syringe needle in a liquid solution of anti-coagulate of blood with the bag in a configuration of substantially reduced dimensions;

withdrawing the syringe plunger with the opening means closed to expand the bag into a configuration of enlarged dimensions and draw the anti-coagulate into the bag chamber;

pushing the syringe plunger into the syringe chamber with the opening means open and compressing the bag into a configuration of reduced dimensions by contact of the plunger on the bag while air passes from the syringe chamber through the opening means without obstruction by the plunger to expel the anti-coagulate from the bag chamber;

withdrawing the syringe plunger with the opening means open to position the plunger at a proximal position of the syringe chamber without expansion of the compressed bag; and positioning the needle tip in a patient's artery with the opening means open to permit passage of blood into the bag chamber while the bag expands responsive to arterial pressure and while air passes through the opening means.

2. The method of claim 1 including the step before said placing step of pushing the syringe plunger into the syringe chamber with the opening means open and compressing the bag into a configuration of reduced dimensions by contact of the plunger in the bag while air passes from the syringe chamber through the opening means without obstruction by the plunger to expel air from the bag chamber.

3. The method of claim 1 including the step after said positioning step of pushing the syringe plunger into the syringe chamber with the opening means open and compressing the bag into a configuration of reduced dimensions by contact of the plunger in the bag while air passes from the syringe chamber through the opening means without obstruction by the plunger to expel blood from the bag chamber.

* * * * *